Figure 1:
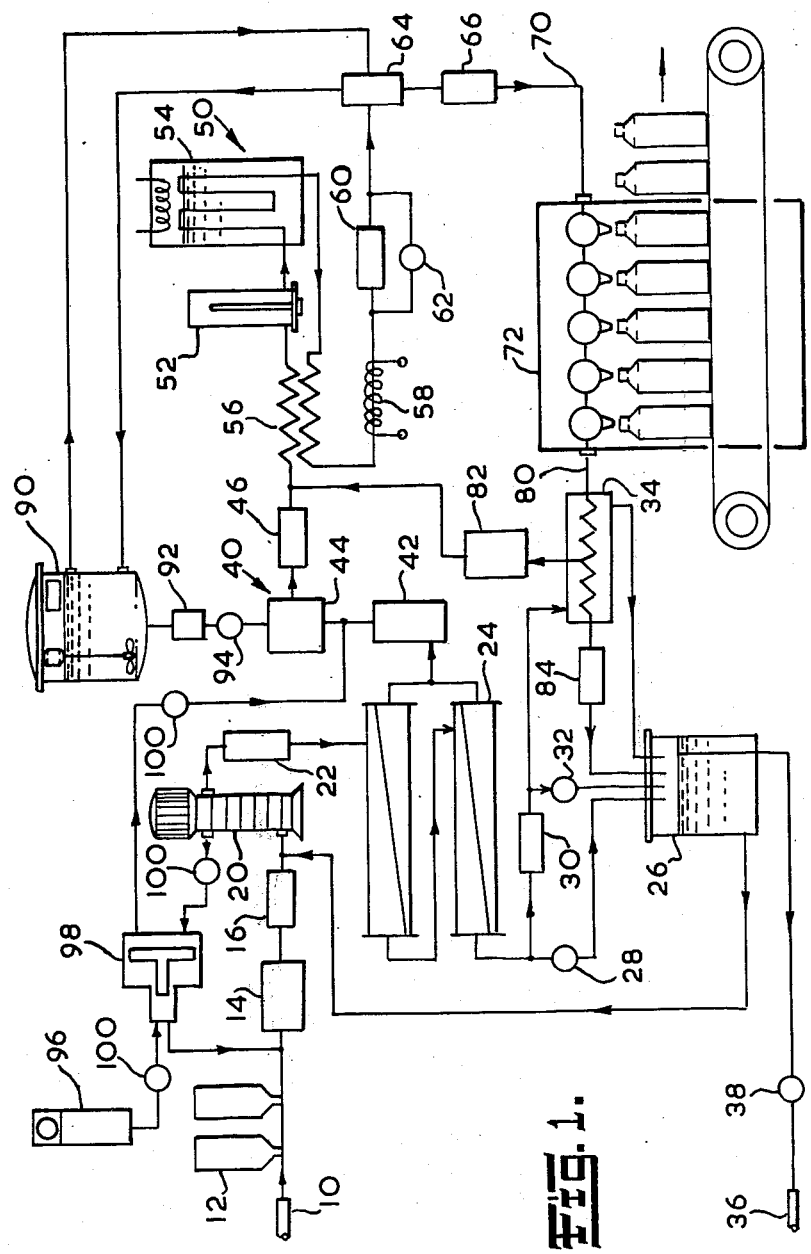

United States Patent [19]

Gow et al.

[11] 4,072,610
[45] Feb. 7, 1978

[54] PRODUCTION OF SOLUTIONS

[75] Inventors: James Gordon Gow; Alan Gordon England, both of Liverpool, England

[73] Assignee: Ingerthorpe Holdings Limited, England

[21] Appl. No.: 573,503

[22] Filed: May 1, 1975

[51] Int. Cl.² .............................................. B01D 31/00
[52] U.S. Cl. .................................. 210/90; 210/96 M; 210/259
[58] Field of Search ............ 210/259, 96 M, 90, 321 B

[56] References Cited
U.S. PATENT DOCUMENTS

| 3,323,649 | 6/1967 | Rusaen | 210/90 |
| 3,441,136 | 4/1969 | Serfass et al. | 210/96 M X |
| 3,545,438 | 12/1970 | Devries | 210/321 R X |
| 3,550,782 | 12/1970 | Veloz | 210/259 X |
| 3,563,381 | 2/1971 | Edelson et al. | 210/321 B X |
| 3,744,636 | 7/1973 | Commarmot | 210/321 B X |
| 3,753,493 | 8/1973 | Mellor | 210/321 B X |
| 3,774,763 | 11/1973 | Yall et al. | 210/259 X |

Primary Examiner—Frank A. Spear, Jr.
Attorney, Agent, or Firm—Beveridge, De Grandi, Kline & Lunsford

[57] ABSTRACT

This invention relates to the production of aqueous solutions of desired concentration for medical purposes which comprises passing water through a reverse osmosis column capable of retaining 100% of pyrogenic materials; and subsequently, in either order, passing the water through a sterilizer capable of eliminating 100% of bacterial material, and admixing, in suitable ratio, the water with a desired material or with a solution of such material of higher concentration than desired to produce said desired concentration solution.

10 Claims, 3 Drawing Figures

PRODUCTION OF SOLUTIONS

The present invention relates to a method of and apparatus for producing aqueous solutions for medical purposes.

Such solutions must be pyrogen free and sterile and must have a low concentration of minerals. It is however inconvenient in many cases for such solutions to be stored at the desired final concentration since this would involve storage of large quantities of liquid much of which is water. It is therefore desirable to store the material or more preferably a concentrated solution thereof and to dilute subsequently. The highly concentrated solutions are made up from sterile pyrogen free water and remain bacteria-free due to their high concentration. Whilst the invention is especially applicable to production of solutions for immediate use to meet the above difficulty, it may also be used to produce solutions which may be stored ready for use.

According to one aspect of the present invention there is provided a method for the production of an aqueous solution of desired concentration for medical purposes characterised in that the method comprises passing water through a reverse osmosis column capable of retaining 100 percent of pyrogenic materials; and subsequently in either order, passing the water through a sterilizer unit capable of eliminating 100 percent of bacterial material, and admixing in suitable ratio, the water with a desired material or with a solution of such material of higher concentration than desired to produce said desired concentration solution.

According to another aspect of the present invention there is provided an apparatus for the production of an aqueous solution of desired concentration for medical purposes, characterised in that the apparatus comprises a reverse osmosis column capable of retaining 100% of pyrogenic material, the outlet from which is connected to, in either order the inlet of a heat steriliser unit capable of eliminating 100% of bacterial material, and a proportioning system.

The heat steriliser unit may be of any convenient type. One preferred form of steriliser unit is a flash steriliser. In the flash steriliser preferably the temperature of the fluid is raised rapidly to about 150° – 160° C for about 1 minute and then cooled to about 40° C.

Preferably the pyrogen-free water from the reverse osmosis column is of preheated in a preheater of the steriliser unit and the pre-heated water is passed to a main steriliser of the steriliser unit in which the water is maintained at a sterilising temperature for sufficient time to sterilise the water, admixing the water being admixed, in a suitable ratio, with a solution of higher concentration than desired either prior to said preheating step or after said sterilising step.

Advantageously the water is preheated to a temperature of substantially 135° C.

Conveniently the higher concentration solution is prepared from water which has undergone the sterilising step.

The water and the concentrated solution may be admixed upstream or downstream of the steriliser unit and the proportioning system may therefore be connected between the outlet from the reverse osmosis column and the inlet to the steriliser unit or alternatively to the outlet from the steriliser unit. The former of these two alternatives is preferred.

In this preferred embodiment pyrogen free water from the reverse osmosis column is delivered to the proportioning system e.g. a proportioning pump and a pyrogen free, mineral free, sterile, concentrated solution of the material required (e.g. glucose or glycine) is separately delivered to the proportioning system, which then delivers solution at the required concentration to the steriliser. One proportioning pump which has been found to be suitable has a delivery rate of up to 1½ liters per minute. The proportioning system may operate in various ways e.g. measured quantities of water and a solution of known concentration may be admixed (as in a proportioning pump) or the concentration of the diluted solution may be constantly measured and the ratio of water to concentrated solution adjusted to give the correctly diluted solution. This latter method is especially useful when the solution is conductive since the conductivity provides a ready measure of concentration.

In osmosis, flow through the semi-permeable membrane is from the less concentrated phase to the more concentrated phase. By applying sufficient pressure on the more concentrated phase this flow may be reversed thereby causing reverse osmosis to occur.

The reverse osmosis column used in the present invention preferably employs a semi-permeable membrane made from a cellulose base material e.g. cellulose acetate. The membrane may be in many different configurations. It has been found however that one or more spirally wound tubes of the membrane, a plurality of tubes of the membrane in parallel relationship or one or more spirally wound tubes of the membrane are especially suitable.

Suitable reverse osmosis columns are produced by Ajax International Corporation; Osmanics Inc. and De Danske Sukkerfabricker A.G. (Membrane type 975 being especially suitable.

Pyrogens are toxic, non dialysable fever producing substances formed by various microorganisms and their exact constitution is at present not known. (The presence of pyrogens in a particular solution is detected by a test involving injecting a sample into a rabbit). Pyrogens are believed however to have molecular weight above 2,000. The reverse osmosis column therefore will probably remove all pyrogens if it has a semi-permeable membrane which prevents passage of materials having a molecular weight of 2,000. It is however preferred that the semi-permeable membrane will prevent passage of all materials with a molecular weight above 1,000 more preferably all materials with a molecular weight of 200 and above. Membrane type 975 mentioned above is capable of preventing passage of materials having a molecular weight of 200 and above.

It is preferable to pass the water through a pre-filter prior to entering the reverse osmosis column and the pre-filter preferably has a pore size between 0.5 and 10 microns, preferably between 0.5 and one micron. This pre-filter is included to protect the reverse osmosis column and is usually a mechanical filter, preferably made of fiber-glass and merely removes relatively large particles.

A pump may be required to maintain an adequate flow rate although in many cases no such pump will be necessary. This applies particularly where the supply of water is taken directly from the mains, since in the majority of cases the mains pressure will be sufficient to maintain an adequate flow rate.

It is preferred that additional safety devices be incorporated. For example a pressure head safety device may be incorporated to ensure correct pressure and/or a bubble test device may be included. Another safety device which is preferably incorporated is a filter between the outlet from the reverse osmosis column and the inlet to the steriliser together with means for measuring the pressure differential between the two sides of the filter. Thus if the reverse osmosis column fails this additional filter will begin to block and the pressure differential between the two sides of the filter will alter considerably. Preferably the apparatus includes one arrangement whereby any alteration in the pressure differential from its normal range causes the apparatus to be switched off. The filter is preferably a surface type filter and a suitable pore size is of the order of $0.2\mu$.

Aqueous solutions from the device of the invention may be used directly or may be stored for subsequent use.

The process of the invention is applicable to production of for example glucose, glycine etc., The aqueous solutions produced in accordance with the invention may be used for various medical purposes, e.g. peritoneal dialysis, bladder irrigation and intravenous use. For bladder irrigation the flow rate through the apparatus of the invention is preferably of the order of 2 liters per minute and for peritoneal dialysis a flow rate of the order of ½ liter per minute is desirable.

The present invention is further described hereinafter, by way of example, with reference to the accompanying drawings which are schematic diagrams of apparatus for producing an aqueous solution of a desired concentration for medical purposes.

Figure 2A:
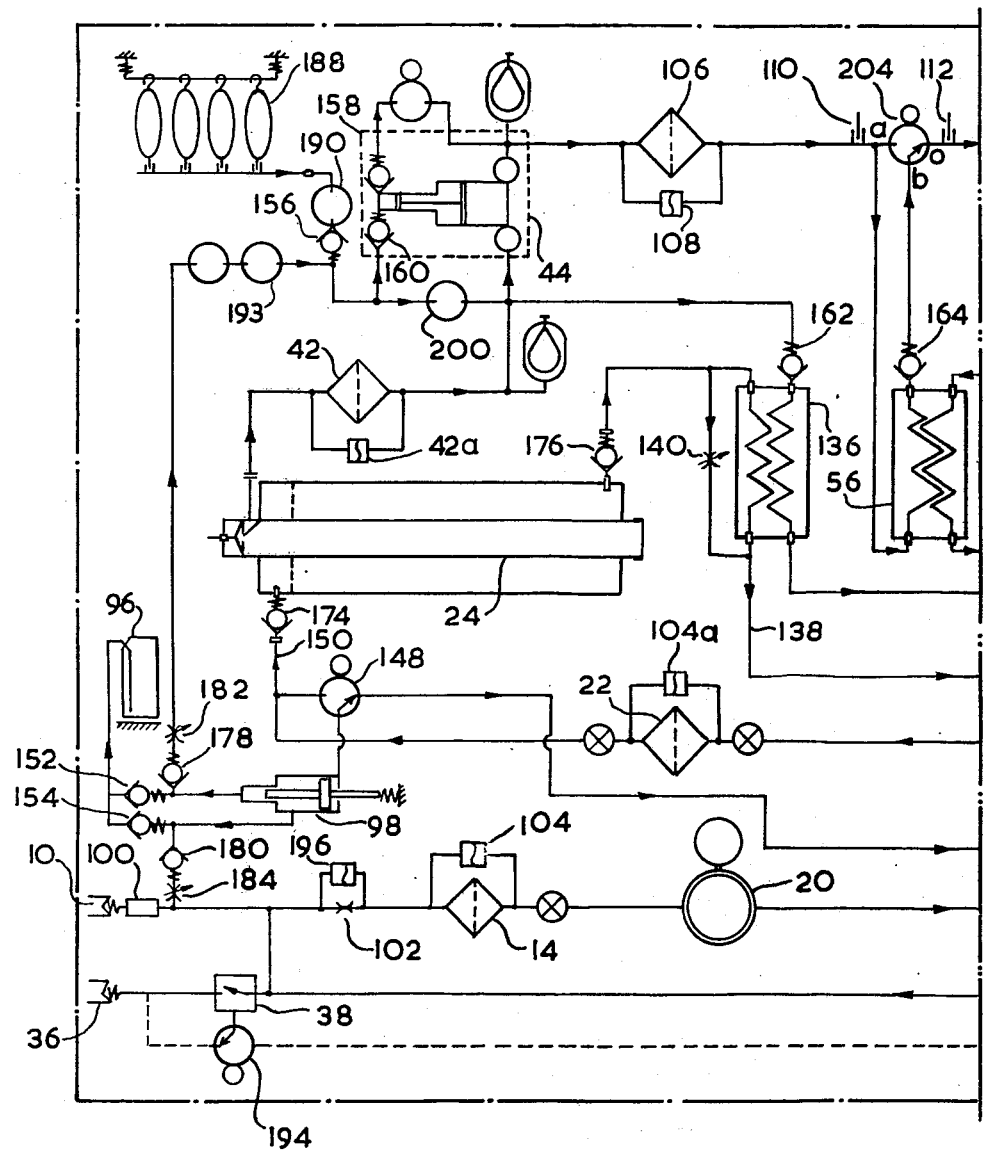
Figure 2B:
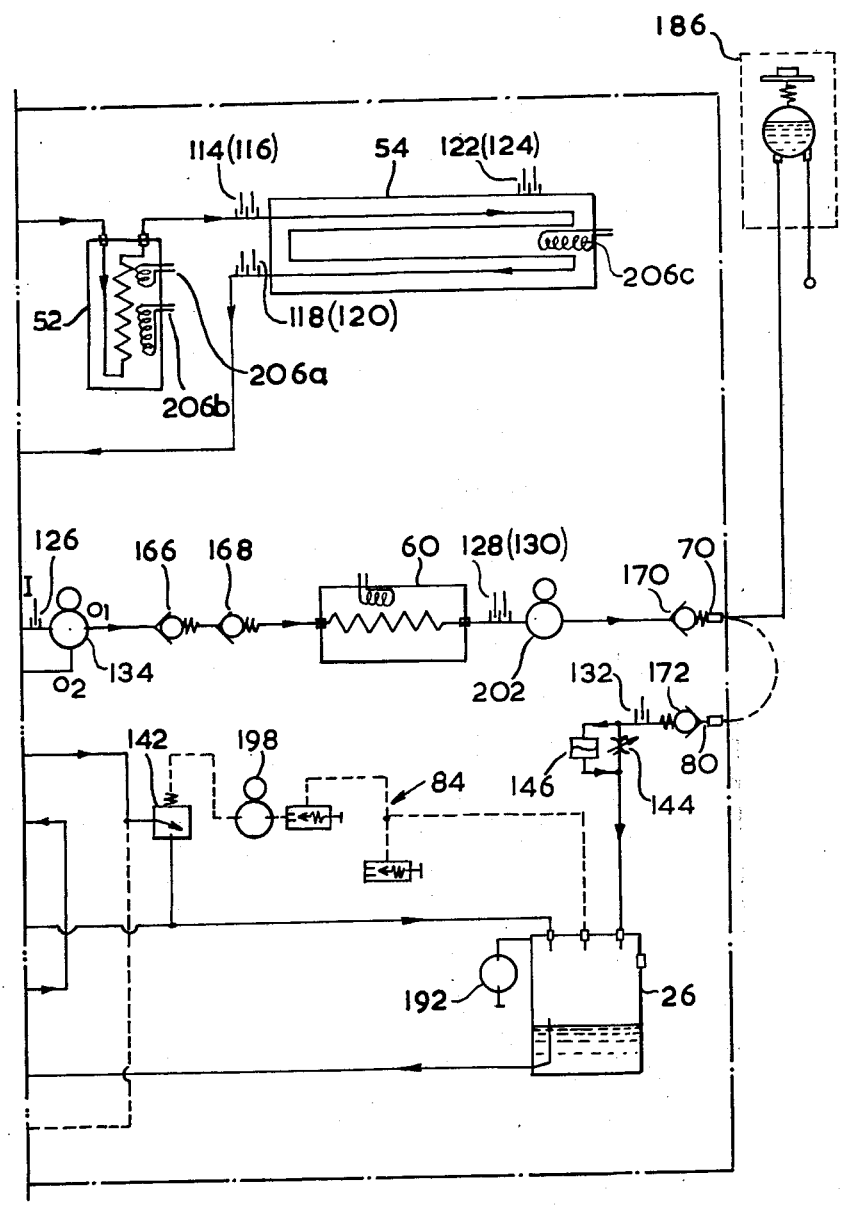

In the drawings:

FIG. 1 is a schematic diagram of a first embodiment of apparatus in accordance with the present invention; and FIGS. 2A and 2B, when aligned side by side with FIG. 2A to the left of FIG. 2B, provide a schematic diagram of a modified form of apparatus in accordance with the present invention.

The apparatus shown in FIG. 1 at the drawing includes an inlet 10 for connection to a source of water (not shown in the drawing) e.g. tap water; a pump 20 which maintains an adequate flow rate of water to two reverse osmosis columns 24 which are capable of retaining 100% of pyrogenic materials; a proportioning system 40 which mixes the pyrogen free water with a pyrogen free, mineral free, sterile, concentrated solution of the material required (e.g. glucose or glycine) and then delivers solution at the required concentration to a heat steriliser 50 which sterilises the solution; and a solution outlet 70 which, in this embodiment, is connected to a bottling plant 72 e.g. a laminar flow filling and capping machine. The aforementioned parts of the apparatus are in the main water flow path through the apparatus. The pump 20 may be omitted if the water pressure from the source is sufficient to maintain an adequate flow rate of water to the reverse osmosis columns 24. Furthermore, although two reverse osmosis columns 24 are shown, the actual number used will depend upon the output flowrate of solution required from the apparatus. Water flows from the inlet 10 by way of a deioniser 12 which deionises the water and a meter 16 for measuring the conductivity of the water to the pump 20, a filter 14 conveniently being provided between the inlet 10 and the pump 20 to filter out material which might damage the pump 20. The deionised water is pumped to the reverse osmosis columns 24 conveniently via a second filter 22 which is included to protect the reverse osmosis columns 24 and is usually a mechanical filter for removing relatively large particles, the filter having a pore size between 0.5 and 10 microns, preferably 1 micron. The high water pressure developed in the reverse osmosis columns 24 by the pump 20 cause the water to permeate through the semi permeable membranes of the columns 24 while the membranes prevent the passage of pyrogenic material. To prevent damage to the reverse osmosis column 24 as a result of pressure build up therein the pyrogen-containing water is fed back to the input of the pump 20 by way of a feedback network which includes a return tank 26. The reverse osmosis columns 24 are connected to the tank 26 by way of three paths one of which is controlled by a valve 28, a second of which is controlled by a pressure responsive valve 30 in series with a valve 32 and a third of which, also controlled by the pressure responsive valve 30, includes a heat exchanger 34 further described hereinafter. The tank 26 also has an overflow connected to an outlet 36 controlled by a valve 38.

Pyrogen free water from the reverse osmosis columns 24 passes preferably through a filter 42 of the proportioning system 40 to a variable ratio mix pump 44. The filter 42 is a safety device with means for measuring the pressure differential between the two sides of the filter. Thus if the reverse osmosis column fails this additional filter will begin to block and the pressure differential between the two sides of the filter will alter considerably. Preferably the apparatus includes an arrangement whereby any alteration in the pressure differential from its normal range causes the apparatus to be switched off. The filter is preferably a surface type filter and a suitable pore size is of the order of $0.2\mu$. The pump 44 mixes the pyrogen free water with the concentrated solution of the material required to produce an aqueous solution of the desired concentration. This desired concentration is monitored by a sensor 46, connected downstream of the pump 44, which controls the pump 44 accordingly to ensure that the desired concentration is maintained.

The pyrogen free solution then flows into the steriliser 50 which comprises a pre-heater 52 for pre-heating the solution to a temperature of approximately 135° C and a main steriliser 54 which is connected downstream of the pre-heater.

The pre-heater is advantageously designed so that the exposure time of the solution to the pre-heating is short and may be in the form of a concentric tube heater. The main steriliser 54 preferably comprises a pipe through which the solution flows and which is immersed in a fluid bath. The pipe is arranged in the bath in a multi-tube parallel flow system so that the solution flowing therethrough is subjected to a sterilising temperature for sufficient time to sterilise the solution, the fluid bath being maintained at for example 138° C. The main steriliser is advantageously an autoclave. Conveniently the sterilised solution is passed through a heat exchanger 56 connected upstream of the pre-heater 52 to further pre-heat solution upstream of the pre-heater 52 e.g. to 90° C. Where the sterilised solution is to be bottled, as in the present example, it is advisable for the sterilised solution to be at or above approximately 80° C to ensure that any bacteria in the bottling plant which might contaminate the solution is killed. To this end a heater 58 is provided downstream of the heat exchanger 56 to heat the cooled solution up to a temperature of approximately 80° C. A pressurising valve 60, which conveniently has a bypass valve 62, is connected downstream of the heater 58 to reduce the risk of the solution boiling, and the valve 60 is connected to the outlet 70 by way of a further valve 64 and a filter 66.

The apparatus also has a further inlet 80 which is connected to an overflow of the bottling plant 72 and enables feed of the overflow solution to the tank 26 and/or the steriliser 50. The heat exchanger 34 is provided to cool the overflow solution to a temperature at which it can be recycled through the steriliser 50 and connects the inlet 80 to a recirculating pump 82 which returns the overflow solution to the main water flow path between the proportioning system and the heat exchanger 56. The heat exchanger 34 also connects the inlet 80 to the tank 26 by way of a pressure relief valve 84.

The pyrogen free, mineral free, sterile, concentrated solution is supplied to the variable ratio mix pump 40 from a vessel 90 conveniently by way of a filter 92 and a valve 94. The vessel 90 is connected in a closed loop from the valve 64 so that it receives only pyrogen free, sterilised solution, and concentrate in the form of a powder charge is added to the solution in the vessel 90 to produce the concentrated solution.

One disadvantage of previous known apparatus for producing aqueous solutions for medical purposes lies in the possibility of bacteria entering the apparatus while it is switched off, particularly at the output 70, and contaminating the solution produced during use of the apparatus. To overcome this disadvantage a reservoir 96 of 1% formulin solution is connected to various parts of the water main flow path by way of an injection pump 98 and valves 100. Immediately the apparatus is switched off the injection pump 98 operates to fill the apparatus with the formalin solution, the latter displacing the water in the apparatus and killing bacteria which enters the apparatus. On switch on of the apparatus the bottling plant is maintained inoperative to allow the water flowing via the inlet 10 to flush the formalin solution out of the apparatus through the drain outlet 36. After a few minutes delay the powder charge is released in the vessel 90 and the bottling plant operated.

Where the outlet 70 is connected to a drip feed for a patient it is essential that the solution supplied should be at the correct temperature, approximately 40° C. The heater 58, and therefore the cooler 34, may be omitted, or alternatively the heater 58 may be used to regulate the solution temperature to approximately 40° C. The outlet 70 and the inlet 80 may then be directly connected.

In further embodiments in accordance with the present invention the vessel 90 is replaced by a source of ready made concentrate solution, and the deioniser 12 may be eliminated if deionised water is supplied to the inlet 10.

The proportioning system may alternatively be connected in the main flow path downstream of the steriliser.

Conveniently the main steriliser is an autoclave, or a flash steriliser in which the water is heated rapidly to 150° C to 160° C for substantially 1 minute.

Pyrogen tests using the apparatus of the present invention were carried out and the trials were designed by the Pharmacological Department of Health and Social Security. In the tests international reference pyrogens were introduced into the system proximal to the columns. In a series of 100 experiments no failures were reported and this fulfils the criteria accepted by the British and European Pharmacopea.

A clinical programme of testing was set up using the apparatus with, as a control, 3 liter pre-sterilised fluid bags containing 1.5% glycine. All patients had a transuerethral resection of the prostate. 47 patients were investigated, 23 on the machine and 24 using the control measures. The temperature was taken half hourly for the first 4 hours to exclude a pyrogenic response and four hourly afterwards for a period of 24 hours.

The urine of all patients was examined immediately prior to operation, one, three and seven days afterwards. The results are shown in the accompanying table.

|  | Machine | Control |
| --- | --- | --- |
| Infective on admission | 1 | 2 |
| 3 days post operative | 1 | 5 |
| 7 days post operative | 3 | 4 |
| Indwelling catheter on admission | 6 | 6 |
| Indwelling catheter with subsequent infection | 1 | 2 |

The results show a greater number of infections in the control series but with the number of patients involved the difference is not statistically significant. It does, however, highlight one essential difference between the two systems. Once a fluid delivery bag is connected to the apparatus by way of an endoscope the bag remains untouched until the operation is completed, but the 3 liter bag system necessitates changes of bags with all the attendant risks of introducing organisms into the patent.

FIG. 2 shows a modified and more detailed form of the apparatus of FIG. 1 particularly useful in drip feed applications. Like parts in the Figs. are given the same reference numeral.

100 is an adjustable non-return pressure control valve which controls the flow rate of the input water. A flow control orifice 102 connects the valve 100 to the filter 14 which has a differential pressure switch 104 connected across it, this providing a check on the actual water flow rate. A similar switch 104a is also connected across the filter 22. The filter 42 also includes means in the form of a further differential pressure switch which monitors the fluid pressure across the filter. A further filter 106 with a differential pressure switch 108 is provided after the proportioning pump 44. Sensors 110 and 112 are provided for monitoring the water temperature upstream and downstream of the heat exchanger 56, further temperature sensors 114 to 132 also being provided to keep a check on the water temperature. Water output from the heat exchanger 56 can be fed back to the proportioning system during operation of the apparatus when no output solution is required by way of a valve 134, preferably a 3 port 2 position valve which normally interconnects the heat exchanger 56 and the heater 60. The valve 134 can, however, be switched to return sterilised solution via a heat exchanger 136 to the proportioning system. The heat exchanger 136 is also connected in a pressure relief line 138 from the reverse osmosis column 24 so that water fed through the relief line 138 to the tank 26 cools the returned solution. A variable orifice valve 140 is connected across the heat exchanger 136 in the relief line 138 to control the water flow rate along this line 138. The line 138 can be connected by a valve 142 either directly to the tank 26 or via the pressurising valve unit 84 (shown dotted).

The input 80 is connected to the tank 26 by way of a variable orifice valve 144 which controls the water flow rate, a differential pressure switch 146 being connected thereacross. The formalin injection pump 98 is normally connected to the tank 26 by way of a valve 148 which, however can connect the pump to the feed line 150 to the column 24.

Valves 152 to 180 are non-return pressure control valves, preferably adjustable, and valves 182 and 184 are variable orifice flow control valves.

The apparatus output 70 is connected firstly to the tank 26 to allow the system to be swilled out and then to the sterile plastic bag set 186. The apparatus of FIG. 2 operates in a similar manner to FIG. 1.

The sterile pyrogen free concentrate is fed to the proportioning pump 44 from container 188 via control valve 190.

The filters 42 and 106 are particulate filters. The filter 42 quickly blocks and thus causes the switch 42a to actuate an alarm when the reverse osmosis column fails and allows particles and thus pyrogen through.

The filter 106 is also a particulate filter which eliminates particles introduced by the proportioning system. All of the differential pressure switches monitor the operation of their various filters and orifices etc.

In the apparatus of FIG. 2 the proportioning pump 44 is electrically driven and thus provides the pressure to maintain a return feed along the line 138 when required.

In a further embodiment, not illustrated, the proportioning pump is a passive pump which is driven by the excess pressure produced by the pump 20 and therefore an additional pump is included in line 138 to provide return flow therealong.

The fluids produced by the process of the invention and also the apparatus in accordance with the invention are useful in the treatment of warm blooded animals, particularly human beings.

In one example the apparatus according to the present invention is used in endoscopic surgery and is connected into a patient's bladder by way of a cystoscope. The solution produced by the apparatus e.g. pure water, dextrose or glycine solutions is used to wash away blood. The solution must of course be iso-osmolar with respect to the patients body fluid.

In a second example of use of the apparatus according to the present invention in the treatment of patients with kidney infections the solution, a dialysate, is fed into the abdominal cavity where it serves to absorb waste products.

The operation of the apparatus of FIG. 2 will be described with reference to the logic table I.

On switch on the solenoid valves 190, 192 and 194 are opened and the switches 196, 104, 104a monitor the water flow through. These switches halt the operation if there is not free unimpeded throughput of water. The solenoid valves 198, 200, 202 then open and the pre-pasteurise warmup phase (heaters 206a and 206b) is initiated by a pressure-operated switch. The output 70 is connected to the input 80.

TABLE 1

|  | 194 | 198 | 192 | 200 | 204 | 134 | 202 | 190 | 193 | 148 | 206a | 206b | 206c | Timer TmB | TmP | TmF | 44 | 20 | P |
|---|---|---|---|---|---|---|---|---|---|---|---|---|---|---|---|---|---|---|---|
| Start | C | C | O | b/o | I/°2 | C | C | C | C | C | Off | Off | Off | Off | Off | Off | Off | On | X |
| Warm Up | O | C | C | b/o | I/°1 | O | C | C | C | C | On | On | Off | Off | Off | Off | On | On | 300 |
| Pasteurise | I/°2 | C | C | a/o | I/°1 | O | C | C | C | C | On | On | Off | Off | On | Off | On | On | 300 |
| Heat Up Prime | I/°2 | C | C | b/o | I/°1 | O | C | C | C | C | On | On | On | Off | Off | off | On | On | 300 |
| Autoclave Prime | I/°2 | C | C | b/o | I/°1 | O | 0 | C | C | On | On | On | Off | On | Off | On | On | 300 |
| Circulate | C | C | O | b/o | I/°2 | C | C | C | C | C | On | On | On | On | On | Off | On | On | low |
| Hold Ready | C | C | O | b/o | I/°2 | C | C | C | C | C | On | On | On | On | Off | Off | On | On | low |
| Fill Headerbag | I/°2 | C | C | b/o | I/°1 | O | O | C | C | On | On | On | Off | Off | Off | On | On | 300 |
| Hold-Bag Full | C | C | O | b/o | I/°2 | C | C | C | C | C | On | On | On | On | Off | Off | On | On | low |
| Replenish Bag | I/°2 | C | C | b/o | I/°1 | O | O | C | C | On | On | On | Off | Off | Off | On | On | 300 |
| Terminate | I/°2 | C | C | b/o | I/°1 | O | C | O | O | Off | Off | Off | Off | Off | On | On | On | 300 |
| Flush Circ. | C | C | O | b/o | I/°, | C | C | C | C | Off | Off | Off | Off | Off | On | On | On | low |
| Switch Off | C | O | O | b/o | I/°2 | C | O | C | C | Off | Off | Off | Off | Off | Off | Off | Off | low |

|  | Microswitches | | | | | | | | | | | | |
|---|---|---|---|---|---|---|---|---|---|---|---|---|---|
|  | 196 | 104 | 104a | 42a | 108 | Conc. | From. | Lev. | Link | Bag | Circ. | Fsn | Psw | Term |
| Start | M | M | M | X | X | M | M | low | M | X | X | M | X | Off |
| Warm Up | M | M | M | M | M | M | M | low | M | X | X | M | M | Off |
| Pasteurise | M | M | M | M | M | M | M | low | M | X | X | M | M | Off |
| Heat Up Prime | M | M | M | M | M | M | M | low | M | X | X | M | M | Off |
| Autoclave Prime | M | M | M | M | M | M | M | low | M | X | X | M | M | Off |
| Circulate | M | M | M | M | M | M | M | low | M | X | X | M | B | Off |
| Hold Ready | M | M | M | M | M | M | M | low | X | X | X | M | B | Off |
| Fill Headerbag | M | M | M | M | M | M | M | low | B | B | On | M | M | Off |
| Hold-Bag Full | M | M | M | M | M | M | M | low | B | M | On | M | B | Off |
| Replenish Bag | M | M | M | M | M | M | M | low | B | B | On | M | M | Off |
| Terminate | M | M | M | M | M | M | M | X | M | X | X | M | M | On |
| Flush Circ. | M | M | M | M | M | M | M | X | M | X | X | B | B | On |
| Switch Off | M | M | M | M | M | X | X | X | M | X | X | M | X | On |

|  | Elapsed time | | | | | | | | |
|---|---|---|---|---|---|---|---|---|---|
|  | $t_b$ | $t_p$ | $t_f$ | 114 | 118 | 128 | 132 | 122 | |
| Start | 0.0 | 0.0 | 0.0 | X | X | X | X | 90 | 1 |
| Warm Up | 0.0 | 0.0 | 0.0 | X | X | X | X | X | 2 |

TABLE 1-continued

| Phase | | | | | | | | | | Note |
|---|---|---|---|---|---|---|---|---|---|---|
| Pasteurise | 0.0 | 0.0 | 0.0 | X | X | X | 90 | X | | 3 |
| Heat Up Prime | 0.0 | 30min | 0.0 | X | X | X | X | X | | 4 |
| Autoclave Prime | 0.0 | 0.0 | 0.0 | 130 | 130 | 40 | X | X | | 5 |
| Circulate | 0.0 | 6min | 0.0 | 130 | 130 | 40 | X | X | | 6 |
| Hold Ready | 60m | 12m | 0.0 | 130 | 130 | 40 | X | X | | 7 |
| Fill Headerbag | 60m | 0.0 | 0.0 | 130 | 130 | 40 | X | X | | 8 |
| Hold-Bag Full | 0.0 | 0.0 | 0.0 | 130 | 130 | 40 | X | X | | 9 |
| Replenish Bag | 60m | 0.0 | 0.0 | 130 | 130 | 40 | X | X | | 10 |
| Terminate | 0 | 0 | 0 | X | X | X | X | X | | 11 |
| Flush Circ. | 0 | 0 | 5 | X | X | X | X | X | | 12 |
| Switch Off | 0 | 0 | 10 | X | X | X | X | X | | 13 |

Key for Table 1
1 Starts only if Water supply present, pre and post filters clean. Autoclave temp: less than 90° C, drain hose clear.
2 Pre pastuerise warm up commences.
3 Pasteurise period initiated.
4 Autoclave heat up commences.
5 Concentrate valve opens.
6 Circulate loop charged.
7 Ready for use, connect to header bag for bag filling.
8 Connection made, outlet nozzle →header bag, press 'circ'.
9 Bag filled.
10 Bag refills and empties on demand.
11 Formalin injection initiated.
12 Circulate loop charged with formalin.
13 Complete electrical shutdown.
O - Open
C - Closed
M - Make
B - BreakL16 X - Condition immaterial When the sensor 132 registers a temperature of approximately 90° C the true pasteurising phase is initiated, in which solenoid valve 204 is energised and the pasteurise timer Tmp actuated. The timer Tmp initiates the autoclave 54 warm up after 30 minutes, valve 204 being deactivated after the pasteurising phase is complete.

The concentrate valve is then opened and the water in the autoclave is displaced by the concentrate solution the sensors 114 and 118 monitoring a temperature of about 130° C and the sensor 128 monitoring 40° C for correct operation, this continues for approxmiately six minutes.

The recirculating loop is then fitted with concentrate solution, this taking a further six minutes and the apparatus then is ready for use and the filling of the storage vessel 186 may commence. The timer Tmb stops the bag filling operation after, at most an hour by recirculating the solution.

When the operation is terminated the timer Tmf initiates the formalin solution injection for about 5 minutes and then shuts off the apparatus.

We claim:

1. An apparatus for the production of an aqueous solution of desired concentration for medical purposes, which comprises a first pump connectible to a source of water, a reverse osmosis column connected to said first pump, said reverse osmosis column being capable of retaining 100% of bacterial material; a heat steriliser capable of eliminating 100% of bacterial material; a proportioning pump for admixing the pyrogen-free water with a desired material or with a solution of such material of higher concentration than desired to provide said desired concentration; first fluid flow means connecting an outlet of said reverse osmosis column to the proportioning pump; second fluid flow means connecting an outlet of said proportioning pump to an inlet of said steriliser; a filter between the outlet from the reverse osmosis column and the inlet to the steriliser and including means for measuring the pressure differential between the two sides of the filter; and a device for switching off the apparatus in the event that during operation the pressure differential between the two sides of the filter varies from its normal range.

2. An apparatus as claimed in claim 1 in which the proportioning pump has a delivery rate of up to 1½ liters per minute.

3. An apparatus as claimed in claim 1 in which the reverse osmosis column has a semi-permeable membrane which prevents passage of materials having a molecular weight of 2,000 and above and preferably above 200.

4. Apparatus as claimed in claim 1 wherein the proportioning pump comprises a variable ratio mix pump for mixing said pyrogen free water with a solution of higher concentration than desired to produce said desired concentration solution, and a sensor connected downstream of the proportioning pump for monitoring the concentration of the proportioning pump output solution, the sensor being operable to control the operation of the pump in dependence upon the monitored concentration.

5. Apparatus as claimed in claim 4 further comprising means for adjusting the temperature of the sterilised, admixed solution of desired concentration to substantially 80° C.

6. Apparatus as claimed in claim 5 wherein said temperature adjustment means comprises a heat exchanger having two flow paths one of which is connected upstream of said pre-heater and the second of which is connected downstream of said main steriliser, and a heater connected downstream of said second flow path and said proportioning system for heating the sterilised, admixed solution to substantially 80° C.

7. Apparatus as claimed in claim 1 further comprising injection means operable responsively to deactivation of the apparatus to displace water in the apparatus with a fluid for killing bacteria.

8. Apparatus as claimed in claim 7 wherein said injection means is an injection pump and said fluid is formalin solution.

9. Apparatus as claimed in claim 1 whose output is connected to a bottling machine for bottling said aqueous solution, an overflow of the bottling machine being connected to a second input of the apparatus for feeding overflow solution into said apparatus upstream of the steriliser, the second input being connected to the steriliser upstream thereof by way of cooling means for reducing the temperature of said overflow solution.

10. An apparatus for the production of an aqueous solution of desired concentration for medical purposes, which comprises a first pump connectible to a source of water, a reverse osmosis column connected to said first pump, said reverse osmosis column being capable of retaining 100% of pyrogenic material; a heat steriliser capable of eliminating 100% of bacterial material; a proportioning pump for admixing the pyrogen-free water with a desired material or with a solution of such material of higher concentration than desired to provide said desired concentration; first fluid flow means connecting an outlet of said reverse osmosis column to one of the heat steriliser and the proportioning pump; second fluid flow means connecting an outlet of said one of the heat steriliser and the proportioning pump to an inlet of the other of the heat steriliser and the proportioning pump; a filter between the outlet from the reverse osmosis column and the inlet to the steriliser and including means for measuring the pressure differential between the two sides of the filter; and a device for switching off the apparatus in the event that during operation the pressure differential between the two sides of the filter varies from its normal range.

* * * * *